United States Patent [19]

Franz

[11] 4,003,912
[45] Jan. 18, 1977

[54] DICARBOXIMIDO-N-PHENYLSUB-STITUTED CARBAMATES AND DERIVATIVES

[75] Inventor: John E. Franz, Crestwood, Mo.

[73] Assignee: Monsanto Company, St. Louis, Mo.

[22] Filed: Mar. 21, 1975

[21] Appl. No.: 561,013

Related U.S. Application Data

[63] Continuation of Ser. No. 368,794, June 11, 1973, abandoned.

[52] U.S. Cl. .................... 260/326.4; 260/281 N; 260/326.27; 260/326.39; 424/268; 424/274
[51] Int. Cl.² ............................. C07D 207/46
[58] Field of Search ......................... 260/326.4

[56] References Cited

UNITED STATES PATENTS 3,882,145   5/1975   Bissinger ................. 260/326.4

FOREIGN PATENTS OR APPLICATIONS 648,454   9/1962   Canada ................. 260/326.4
648,453   9/1962   Canada ................. 260/326.4
473,118   5/1969   Switzerland ............ 260/326.4

*Primary Examiner*—Donald G. Daus
*Assistant Examiner*—David E. Wheeler
*Attorney, Agent, or Firm*—William I. Andress; Donald W. Peterson

[57] ABSTRACT

The Dicarboximido-N-Monosubstituted Carbamates of this invention are pesticidally active and particularly useful as herbicides.

9 Claims, No Drawings

DICARBOXIMIDO-N-PHENYLSUBSTITUTED CARBAMATES AND DERIVATIVES

This is a continuation of application Ser. No. 368,794 filed June 11, 1973, now abandoned.

This invention relates to new and useful dicarboximido-N-monosubstituted carbamates of the formula.

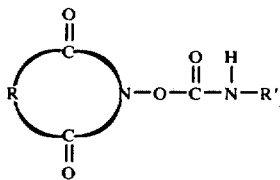

wherein R is ethylene, substituted ethylene, 5-norbornene, 1,2-phenylene, substituted 1,2-phenylene, 1,8-naphthylene or substituted 1,8-naphthylene and R' is alkyl, substituted alkyl, cyclohexyl, phenyl or substituted phenyl.

A preferred substituted phenyl group has the formula

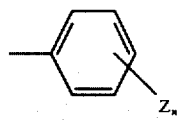

wherein each Z is independently halo, trihalomethyl, cyano, nitro, lower alkyl or lower alkoxy, and $n$ is an integer from 1 through 3, inclusive, provided that when each Z is nitro, n cannot exceed 2. Preferred Z groups are halo, nitro, lower alkyl, trifluoromethyl and lower alkoxy. The term "halo" designates a halogen atom selected from fluorine, chlorine, bromine and iodine.

A preferred substituted 1,2-phenylene group has the formula

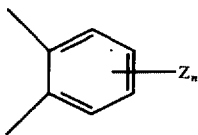

wherein Z and $n$ have the aforementioned significance.

A preferred substituted 1,8-naphthylene group has the formula

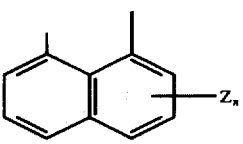

wherein Z and $n$ have the aforementioned significance.

A preferred substituted alkyl group has the formula $-C_xH_{2x-y+1}R''_y$ wherein R'' is halo, phenyl, or substituted phenyl, $x$ is an integer from 1 through 18, inclusive, more preferably 1 through 5, inclusive, and $y$ is an integer from 1 through 3, inclusive.

In a preferred substituted ethylene group from 1 to 4 of the hydrogen atoms are replaced by substituents selected from phenyl, substituted phenyl or halo provided that not more than one substituent is phenyl or substituted phenyl.

As employed herein, the terms "lower alkyl" and "lower alkoxy" designate those groups wherein the aliphatic chain is straight or branched and has from 1 through 5 carbons, inclusive.

The compounds of this invention are conveniently and efficiently prepared by the reaction, in an organic solvent, such as tetrahydrofuran, and in the presence of a trialkylamine, of about equimolecular proportions of an N-hydroxydicarboximide of the formula

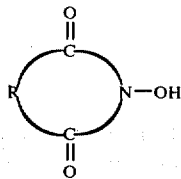

and an isocyanate of the formula

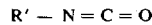

$$R' - N = C = O$$

wherein R and R' have the aforementioned significance.

The amount of trialkyl amine present in the reaction mass is not critical. Usually the trialkylamine is present only in a catalytic amount. It is preferred not to use large quantities, i.e. more than one percent of the reaction mass, if maximum yield of product is desired. Preferred trialkyl amines have from 2 through 5 carbons in the alkyl group. A more preferred trialkyl amine is triethylamine.

The type of organic solvent is not critical so long as the reaction mass is maintained in solution. The reactants are either known compounds or may be prepared from known compounds by known methods.

The reaction is normally carried out at a temperature above the freezing point of the system but preferably not above its boiling point. More preferably, the reaction is carried out at temperatures of from about 0° Centrigrade (°C.), to about 60° C. The reaction is most conveniently carried out at about room temperature, about 23° C. The reaction is usually carried out at atmospheric pressure, but higher or lower pressures may be utilized if equipment and other factors favor such higher or lower pressures. The reaction may be carried out in an open vessel as well as under reflux.

The compounds of this invention are useful as biocides. Exemplary of such biocidal uses for these products is the control of nematodes, arachnids, arthropods and insects as well as eradication of noxious weeds. These compounds are particularly useful as herbicides.

Herbicidal compounds are useful in the selective killing of weeds in crops. In using the compounds of the present invention as pre-emergent and contact herbicides, the compounds can be used alone or in combination with a material referred to in the art as an adjuvant in liquid or solid form. Herbicidal formulations are prepared by admixing the compound which is the active ingredient of the formulation with an adjuvant including diluents, extenders, carriers and conditioning agents to provide compositions in the form of finely-divided particulate solids, granules, pellets, solutions, dispersions or emulsions. Thus, the active ingredient can be used with an adjuvant such as a finely-divided particulate solid, a liquid of organic origin, water, a wetting agent, dispersing agent, an emulsifying agent or any suitable combination of these. The herbicidal formulations usually contain from about 0.1 to about 99 percent by weight of the active ingredient. Application of these formulations to the soil or growth media can be carried out by simply admixing with the soil, by applying to the surface of the soil and thereafter dragging or discing into the soil to the desired depth, or by employing a liquid carrier to accomplish the penetration and impregnation. The application of liquid and particulate solid herbicidal formulations to the surface of soil or to above ground portions of plants can be carried out by conventional methods, e.g. power dusters, boom and hand sprayers and spray dusters. The formulations can also be applied from airplanes as a dust or a spray because of their effectiveness at low dosages. In a further method, the distribution of the active ingredients in soil can be carried out by admixture with the water employed to irrigate the soil. In such procedures, the amount of water can be varied with the porosity and water holding capacity of the soil to obtain the desired depth of distribution of the active ingredients.

The exact amount of active ingredient to be employed is dependent upon the response desired in the plant as well as such other factors as the plant species and stage of development thereof, the specific soil and depth at which the active ingredients are distributed in the soil and the amount of rainfall as well as the specific active ingredient employed. In foliar treatment, the active ingredients are applied in amounts from about 1 to about 50 or more pounds per acre. In aplications to soil for the control of the growth of germinant seeds, germinative seeds, emerging seedlings and established vegetation, the active ingredients are applied in amounts from about 0.1 to about 25 or more pounds per acre. It is believed that one skilled in the art can readily determine from the teachings of this specification the general procedure for any application.

As illustrative of this invention, but not limitative thereof, is the following:

EXAMPLE 1

To a suitable reaction vessel is charged approximately 55 milliliters (ml.) of dry tetrahydrofuran. Approximately 4.6 grams (g.), about 0.04 moles, of N-hydroxysuccinimide is dissolved in the tetrahydrofuran. Approximately 4.8 g., about 0.04 moles, of chloroacetyl isocyanate and one drop of triethyl amine are added. The mass is stirred for about 15 minutes at ambient room temperature, about 23° C. Upon cooling in ice, white crystals form. After separation by filtration, the white crystals are washed with diethyl ether and dissolved in 100 ml. of warmed acetone. 100 ml. of diethyl ether is added and the mixture is cooled. The white crystals which form are recovered by filtration and found to be soluble in dimethyl formamide and acetone, to be insoluble in water, ether, benzene, chloroform, ethyl acetate, and heptane, and to have a melting point of about 171.5° to 174° C. with decomposition and is identified by nuclear magnetic resonance as succinimido-N-chloroacetyl carbamate

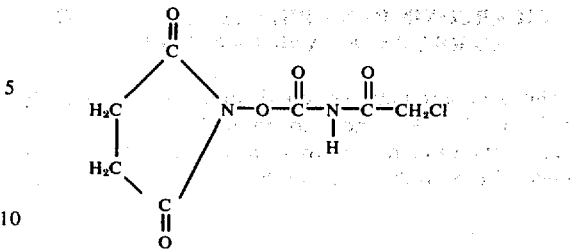

Calculated for $C_7H_7ClN_2O_5$: C,35.84; H, 3.01; Cl, 15.11; N, 11.94. Found: C, 35.98; H, 3.04; Cl, 14.91; N, 11.73.

EXAMPLE 2

To a suitable reaction vessel is charged about 30 ml. of dry tetrahydrofuran. Approximately 2.3 g., about 0.02 moles, of N-hydroxysuccinimide is dissolved in the tetrahyrdofuran at room temperature. Approximately 2.74 g., about 0.02 moles, of ortho-fluorophenyl isocyanate is then added with swirling. Three drops of triethylamine is added and the mass is stirred for a short time at room temperature. The tetrahydrofuran is then removed by heating under reduced pressure leaving a colorless viscous oily residue of about 5.5 g. The residue is extracted with cold diethyl ether giving, upon drying, about 4.0 g. of a fine white powder. The powder is found to be soluble in hot ethanol, acetone, ethyl acetate, chloroform, hot ether and benzene and to have a melting point of about 127° to 128° C. with decomposition and is identified by nuclear magnetic resonance as succinimido-N-(ortho-fluorophenyl) carbamate

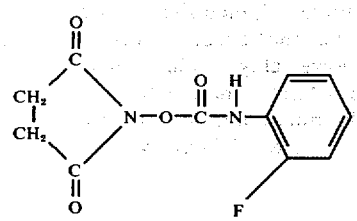

Calculated for $C_{11}H_9FN_2O_4$: C, 52.39; H, 3.60; F, 7.53; N, 11.11. Found: C, 52.12; H, 3.61; F, 7.44; N, 10.97.

EXAMPLE 3

To a suitable reaction vessel is charged about 25 ml. of dry tetrahydrofuran. Approximately 1.8 g., about 0.01 moles, of N-hydroxy-5-norbornene-2,3-dicarboximide is dissolved in the dry tetrahydrofuran. Approximately 0.6 g., about 0.01 moles, of methyl isocyanate and one drop of triethyl amine are then added. The mass is allowed to stand for 5 days at ambient room temperature. A small amount of sediment is noted and removed by centrifugation. The tetrahydrofuran is then removed by distillation under reduced pressure leaving a white powdery residue in the amount of about 2.3 g. The residue is dissolved in hot ethyl acetate and, upon cooling, a white powder crystallizes out of the solution. The white powder is separated from the liquid by filtration and is recovered in the amount of about 1.3 g. The recrystallized white powder is found to be soluble in acetone, benzene, dimethyl formamide, ethanol, hot ethyl acetate and chloroform, to be insoluble in water, ether and heptane, and to have a melting point of about 188.5° to 189° C. with decomposition and is identified by nuclear magnetic resonance as 5-norbornene-2,3-dicarboximido-N-methyl carbamate

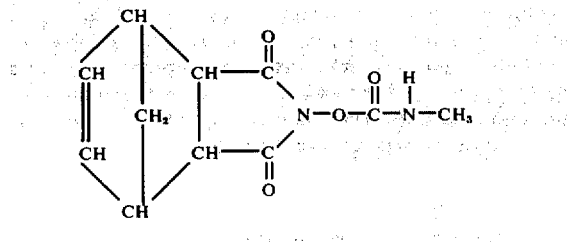

Calculated for $C_{11}H_{12}N_2O_4$: C, 55.93; H, 5.12; N, 11.86. Found: C, 56.25; H, 5.38; N, 11.77.

EXAMPLE 4

To a suitable reaction vessel is charged about 25 ml. of dry tetrahydrofuran. Approximately 1.07 g., about 0.005 moles, of N-hydroxynaphthalimide is added to the tetrahydrofuran. Approximately 0.4 g., about 0.007 moles, of methyl isocyanate and 1 drop of triethyl amine as catalyst are then added with swirling. The mass is allowed to stand for about 4 days at ambient room temperature. A white solid which forms in the reaction mass eventually turns color to tan. The solid is removed by filtration and washed twice with diethyl ether. The tetrahydrofuran and diethyl ether are then removed from the filtrate by distillation leaving a residue. The washed solid and residue are recrystallized from about 125 ml. of hot tetrahydrofuran. The solid is recrystallized again from about 200 ml. of hot ethyl acetate. The resultant ivory solid is found to be soluble in hot ethanol, dimethyl formamide, hot tetrahydrofuran, hot benzene, hot ethyl acetate and hot acetone, and to be insoluble in water, heptane, chloroform, and diethyl ether. The solid has a melting point of about 275° to 276° C. with decomposition and is identified by nuclear magnetic resonance as 1,8-naphthalimido-N-methylcarbamate

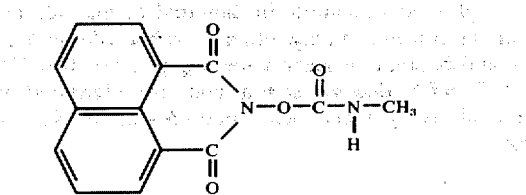

EXAMPLE 5

To a suitable reaction vessel is charged about 20 ml. of dry tetrahydrofuran. Approximately 1.63 g., about 0.01 moles, of N-hydroxyphalimide is dissolved in the dry tetrahydrofuran. Approximately 0.6 g., about 0.01 moles, of methyl isocyanate and a drop of triethylamine are then added. The mass is allowed to stand for about 2 days at ambient room temperature. Colorless, fine needle-like crystals appear and are removed by centrifugation. The crystals are washed twice with diethyl ether and recrystallized from about 75 ml. of hot ethyl acetate. The fine needle-like crystals are again recrystallized from ethyl acetate and dried at 80° C. and 0.3 mm of Hg pressure for about 2 hours. The white needles are found to be soluble in ethanol, dimethyl formamide and acetone, to be insoluble in water, diethyl ether, benzene, chloroform, ethyl acetate and heptane and to have a melting point of about 217° to 218° C. with decomposition. The product is identified by nuclear magnetic resonance as phthalimido-N-methylcarbamate

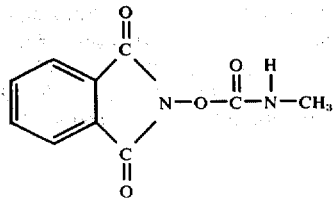

Calculated for $C_{10}H_8N_2O_4$: C, 54.55; H, 3.66; N, 12.72. Found: C, 54.56; H, 3.62; N, 12.70.

EXAMPLE 6

To a suitable reaction vessel is charged about 20 ml. of dry tetrahydrofuran. Approximately 1.15 g., about 0.01 moles, of N-hydroxysuccinimide is dissolved in the tetrahydrofuran by swirling. Approximately 0.6 g., about 0.01 moles, of methyl isocyanate and one drop of triethyl amine are added. The mass is swirled and allowed to stand for about 3 days at ambient room temperature. Dense, colorless plate-like crystals appear and are removed by centrifugation. The recovered crystals are washed with two portions of diethyl ether. Upon cooling the tetrahydrofuran and diethyl ether mixture in ice, a granular solid precipitates and is recovered by filtration. The filtrate is concentrated to near dryness causing further solids to precipitate which are recovered by centrifugation and washed with diethyl ether. Upon recrystallization of the combined solids in 25 mls. of boiling ethyl acetate and recovery by centrifugation, the white crystals are found to be soluble in acetone, ethanol and dimethyl formamide, slightly soluble in chloroform and insoluble in water, diethyl ether, benzene and heptane, to have a melting point of about 157° to 159° C. and identified by nuclear magnetic resonance as succinimido-N-methylcarbamate

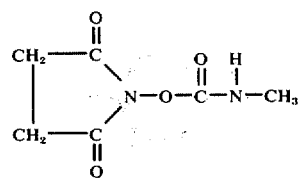

Calculated for $C_6H_8N_2O_4$: C, 41.86; H, 4.68; N, 16.27. Found: C, 41.78; H, 4.48; N, 16.22.

EXAMPLE 7

To a suitable reaction vessel is charged about 50 ml. of dry tetrahydrofuran. Approximately 3.47 g., about 0.03 moles, of N-hydroxysuccinimide is dissolved in the tetrahydrofuran with warming. Approximately 3.59 g., about 0.3 moles, of phenyl isocyanate is added in portions. Three drops of triethylamine are then added. The mass is stirred for about 30 minutes at room temperature. The solution is filtered to remove sediment. About 50 ml. of diethyl ether is added to filtrate. Upon cooling in ice and scratching, a white crystalline powder forms. The powder is recovered by filtration. The filtrate is concentrated to about one half its volume and cooled for 1 hour causing a precipitate to form. The precipitate is recovered by filtration and combined with the recovered powder. The combined materials are recrystallized from boiling ethyl acetate. The white crystals are found to be soluble in hot ethyl acetate, acetone, hot benzene, hot ethanol and dimethyl formamides, slightly soluble in diethyl ether and chloroform, insoluble in water, to have a melting point of about 158° to 160° C. with decomposition and identified by nuclear magnetic resonance as succinimido-N-phenyl-carbamate

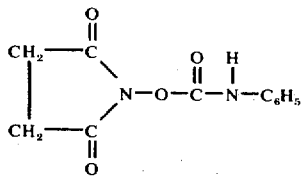

Calculated for $C_{11}H_{10}N_2O_4$: C, 56.41; H, 4.3; N, 11.96. Found: C, 56.28; H, 4.47; N, 11.74.

EXAMPLE 8

To a suitable reaction vessel is charged about 50 ml. of dry tetrahydrofuran. Approximately 3.46 g., about 0.03 moles, of N-hydroxysuccinimide is dissolved in the tetrahydrofuran. Approximately 5.64 g., about 0.03 moles, of 3,4-dichlorophenyl isocyanate is added as a solid in portions. Three drops of triethyl amine are then added. After about 15 minutes of stirring at room temperature the exothermic reaction is complete. The solvent is removed by distillation leaving a crude white powder. The powder is recrystallized twice from boiling ethyl acetate and dried. The white crystals are found to be soluble in acetone, hot benzene, hot ethyl acetate, hot ethanol and dimethyl formamide, slightly soluble in diethyl ether and insoluble in water, chloroform and heptane, to have a melting point of about 188.5° to 191° C. with decomposition and is identified by nuclear magnetic resonance as succinimido-N-(3,4-dichlorophenyl) carbamate

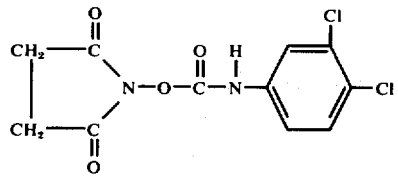

EXAMPLE 9

To a suitable reaction vessel is charged about 50 ml. of dry tetrahydrofuran. Approximately 5.75 g., about 0.05 moles, of N-hydroxysuccinimide are dissolved in the tetrahydrofuran with warming. Approximately 4.25 g., about 0.05 moles, of isopropyl isocyanate in portions. Five drops of triethyl amine are added. The mass is then stirred for about 30 minutes at room temperature. Crystals begin to appear. The solvent is removed by filtration leaving a white powder. The powder is washed well with diethyl ether. The powder is dissolved in 50 ml. of boiling ethyl acetate. The solution is allowed to stand overnight at ambient room temperature and then is cooled in ice. The precipitate which forms is separated from the ethyl acetate by filtration with suction. Upon recrystallization from tetrahydrofuran in this same manner, the white powder is found to be soluble in acetone, chloroform, hot ethanol, hot ethyl acetate and dimethyl formamide, slightly soluble diethyl ether and insoluble water and heptane, to have a melting point of about 144° to 146° C. with decomposition and is identified by nuclear magnetic resonance as succinimido-N-isopropyl carbamate

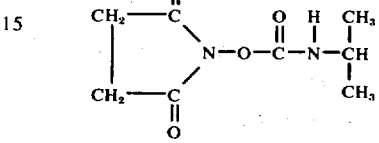

Calculated for $C_8H_{12}N_2O_4$: C, 48.0; H, 6.04; N, 13.99. Found: C, 48.17; H, 6.19; N, 13.81.

EXAMPLE 10

To a suitable reaction vessel is charged approximately 50 ml. of dry tetrahydrofuran. Approximately 3.46 g., about 0.03 moles, of N-hydroxysuccinimide is dissolved in the tetrahydrofuran. Approximately 8.85 g., about 0.03 moles, of octadecyl isocyanate are added in portions. After the addition of 4 drops of triethyl amine, the mass is then stirred for about 30 minutes at ambient room temperature. Thereafter the tetrahydrofuran is removed by filtration leaving white crystals. The crystals are washed with diethyl ether. Upon addition of the ether to the tetrahydrofuran a precipitate appears and is removed by filtration and combined with the first crop of crystals. The combined crops are dissolved in 60 ml. of boiling tetrahydrofuran and, upon slow cooling to room temperature, a white solid crystallizes which is removed by filtration. After second recrystallization from boiling tetrahydrofuran the white opalescent plate-like crystals are found to be slightly soluble in acetone, hot ethanol, hot chloroform, and hot ethyl acetate, soluble in dimethyl formamide and insoluble in water, diethyl ether, tetrahydrofuran, benzene and heptane, to have a melting point of 106.5° to 108° C. with decomposition and are identified by chemical analysis as succinimido-N-octadecylcarbamate

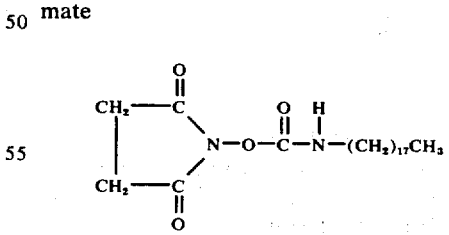

Calculated for $C_{23}H_{42}N_2O_4$: C, 67.28; H, 10.31; N, 6.82. Found: C, 67.10; H, 10.46; N, 6.64.

EXAMPLE 11

To a suitable reaction vessel is charged about 75 ml. of dry tetrahydrofuran. Approximately 5.75 g., about 0.05 moles, of N-hydroxysuccinimide is dissolved in the tetrahydrofuran at room temperature. Approximately 4.95 g., about 0.05 moles, of tertiary-butyl isocyanate is then added in portions with swirling. After addition of 4 drops triethyl amine the mass is stirred for about 30 minutes and then allowed to stand for about two hours at ambient room temperature. A tan residue is then removed by filtration and the tetrahydrofuran is stripped from solution by heating under reduced pressure leaving a white powder in the amount of about 9.8 g. The powder is dissolved in approximately 500 ml. of boiling diethyl ether A portion of the powder does not dissolve and is removed by filtration. The remaining solution is cooled on ice for about 1 hour. A precipitate in the form of fine white needles appears and is separated by filtration. The white needle-like crystals are found to be soluble in acetone, tetrahydrofuran, hot diethyl ether, hot benzene, hot ethyl acetate, ethanol and dimethyl formamide, to be insoluble in water and heptane and to have a melting point of about 149.5° to 151° C. and is identified as succinimido-N-tertiary butylcarbamate

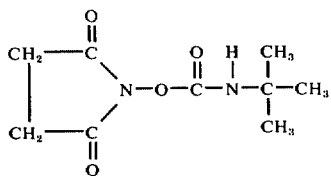

Calculated for $C_9H_{14}N_2O_4$: C, 50.46; H, 6.59; N, 13.08. Found: C, 50.46; H, 6.66; N, 12.92.

EXAMPLE 12

To a suitable reaction vessel is charged about 50 ml. of dry tetrahydrofuran. Approximately 3.46 g., about 0.03 moles, of N-hydroxysuccinimide is dissolved in the dry tetrahydrofuran. In portions, approximately 4.59 g., about 0.03 moles, of meta-chlorophenyl isocyanate and four drops of triethyl amine are then added. A slight exotherm is noted. The mass is swirled for about 15 minutes at room temperature. The tetrahydrofuran is then removed from the reaction mass by distillation leaving about 7.8 g. of a white powdery residue. The residue is dissolved in about 50 ml. of hot ethyl alcohol and upon cooling in ice, a white powder crystallizes out of the solution. The white powder is separated from the liquid by filtration and is recrystallized again. The recrystallized white powder is dried for about 2 hours at about 68° C. and found to be soluble in acetone, ethyl acetate, hot benzene, hot ethanol, dimethyl formamide and chloroform, to be insoluble in water, dimethyl ether and heptane, and to have a melting point of about 134° to 137° c. with decomposition and is identified as succinimido-N-(meta-chlorophenyl) carbamate

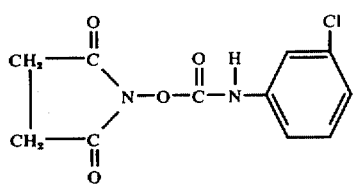

Calcualted for $C_{11}H_9ClN_2O_4$: C, 49.18; H, 3.38; Cl, 13.2; N, 10.43. Found: C, 49.01; H, 3.47; Cl, 13.04; N, 10.35.

EXAMPLE 13

To a suitable reaction vessel is charged about 50 ml. of dry tetrahydrofuran. Approximately 3.46 g., about 0.03 moles, of N-hydroxysuccinimide is dissolved in the tetrahydrofuran. Approximately 5.4 g., about 0.033 moles, of para-ethoxyphenyl isocyanate of about 90% purity and 4 drops of triethyl amine as catalyst are then added. An exotherm is noted. The mass is swirled for about 15 minutes at room temperature. The tetrahydrofuran is then removed from the filtrate by distillation leaving an ivory residue. The residue is dissolved by heating in about 50 ml. of ethyl acetate. The solution is boiled and filtered hot to remove sediment. Upon cooling, a white solid slowly crystallizes out of the solution. The white powder is separated from the solution by filtration and recrystallized out of ethyl acetate again to a constant melting point of about 158° to 159° C. with decomposition. The powder is dried at 68° C. and 0.2 mm of Hg. pressure for about 2 hours and found to be soluble in hot ethanol, hot benzene, hot ethyl acetate, dimethyl formamide, tetrahydrofuran, hot chloroform and acetone, to be insoluble in water, heptane and dimethyl ether and to have a melting point of about 158° to 159° C. with decomposition and is identified as succinimido-N-(4-ethoxyphenyl) carbamate

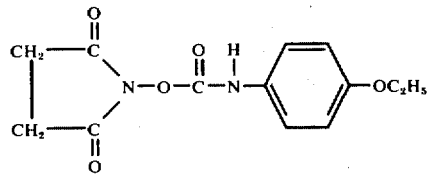

Calculated for $C_{13}H_{14}N_2O_5$: C, 56.11; H, 5.07; N, 10.07. Found: C, 55.93; H, 5.14; N, 9.94.

In a similar manner by dissolving one molecular proportion of the appropriate N-hydroxydicarboximide in dry tetrahydrofuran, adding the appropriate isocyanate in an equimolecular amount in the presence of a catalytic amount of triethyl amine, and then separating the resultant product by conventional means, dicarboximido-N-monosubstituted carbamates of the formula

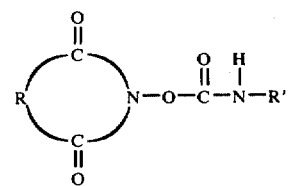

are obtained wherein R and R' are as shown:

| Example | R | R' |
|---|---|---|
| 14. | —CHCl—CHCl— | 3-nitrophenyl |
| 15. | —CH₂—CH(C₆H₅)— | —CHCl—CH₂Cl |
| 16. | —CH(C₆H₄-2-CF₃)—CH₂— | 4-bromophenyl |
| 17. | —CCl₂—CH(C₆H₅)— | 2,6-di(n-butoxy)phenyl |
| 18. | —CF₂—CF₂— | phenyl |
| 19. | —CHBr—CBr₂— | —(CH₂)₁₁CH₃ |
| 20. | 3,4-dinitrophenyl | —CH₂C₆H₅ |
| 21. | 2,4,5-trichlorophenyl | —CH₂—C₆H₄-4-Br |
| 22. | 4-(CF₃)phenyl | —(CH₂)₅CH₂Br |
| 23. | 2,6-di(isopropoxy)phenyl | —CF₃ |
| 24. | 2-bromo-4-methylphenyl | 2-cyanophenyl |
| 25. | 1,8-dimethyl-2-(n-butoxy)naphthyl | 4-(n-propoxy)phenyl |
| 26. | 4,5-dichloro-1,8-dimethylnaphthyl | —(CH₂)₇CH₃ |
| 27. | 6-(CF₃)-naphthyl | 2,4,6-trichlorophenyl |

| Example | R | R' |
|---|---|---|
| 28. | 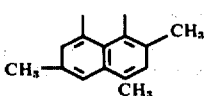 | 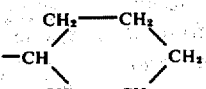 |
| 29. | 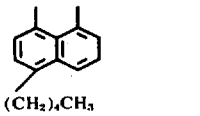 | 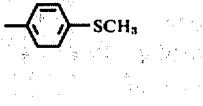 |
| 30. | 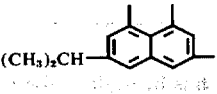 | 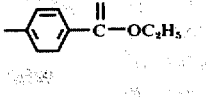 |
| 31. | 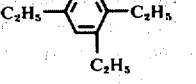 |  |
| 32. | 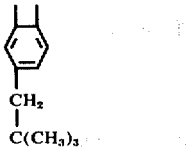 | 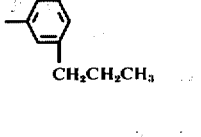 |
| 33. | 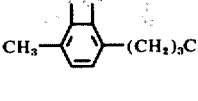 | 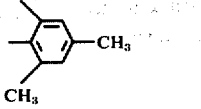 |

EXAMPLE 34

Pre-emergent herbicidal activity of representative compounds of this invention is determined by the following procedure:

A good grade of top soil is placed in aluminum pans and compacted to a depth of ⅜ to ½ inch from the top of the pan. A predetermined number of seeds of each of several plant species are placed on top of the soil in the pans. The seeds are covered with soil and the pans leveled. The herbicidal composition is applied by spraying the surface of the top layer of soil with a solution containing a sufficient amount of active ingredient to obtain the desired rate of application which is measured in terms of lbs. per acre. The pans are then placed on a sand bench in the greenhouse and watered from below as needed. The plants are observed at the end of approximately 14 days and the results recorded.

The pre-emergent phytotoxic activity of the active ingredients is measured by the average percent control of each seed lot. The average percent control is converted to a relative numerical scale for the sake of brevity and simplicity in the examples. The pre-emergent phytotoxic activity index, as used in Table I, is defined as follows:

| Average Percent Control | | Numerical Scale |
|---|---|---|
| 0 – 25 | = | 0 |
| 26 – 50 | = | 1 |
| 51 – 75 | = | 2 |
| 76 – 100 | = | 3 |

The pre-emergent phytotoxic activity of some of the compounds of this invention are summarized in Table I. A dash (-) denotes that the species is not in the test.

TABLE I

| Compound of Example No. | 2 | 6 | 7 | 8 | 9 | 11 |
|---|---|---|---|---|---|---|
| Rate of Application (lbs./acre) | 5 | 10 | 5 | 5 | 5 | 5 |
| Plant Species | | | | | | |
| Canada thistle | 1 | — | 1 | 0 | 0 | 1 |
| Cocklebur | 2 | 1 | 0 | 3 | 0 | 1 |
| Velvet leaf | 1 | 0 | 0 | 2 | 0 | 0 |
| Morning glory | 0 | 1 | 2 | 1 | 2 | 1 |
| Lambsquarters | 3 | 3 | 2 | 3 | 0 | 0 |
| Smartweed | 0 | — | 2 | 3 | 1 | 2 |
| Nutsedge | 0 | 0 | 1 | 1 | 2 | 0 |
| Quackgrass | 0 | 1 | 1 | 0 | 1 | 0 |
| Johnsongrass | 3 | 0 | 0 | 0 | 0 | 1 |
| Brome | 0 | 0 | 0 | 0 | 0 | 0 |
| Barnyard Grass | 0 | 1 | 1 | 1 | 0 | 0 |

EXAMPLE 35

Contact herbicidal activity of representative compounds of this invention is determined by the following procedure:

The compound to be tested is applied in spray form to plants of a given age of several grasses and broadleaf species. After the plants are the desired age, each aluminum pan of plants is sprayed with a given volume of a solution of the desired percent concentration of the candidate chemical. This solution is prepared from an aliquot of a 2 percent solution of the candidate compound in acetone, a known amount of cyclohexanone-emulsifying agent mix, and sufficient water to make up to volume. The emulsifying agent is a mixture comprising 35 wt. percent of a tall oil-ethylene oxide condensate having about 6 moles of ethylene oxide per mole of tall oil. The injuries to the plants are then observed approximately 14 days later and the results are recorded. The herbicidal rating is obtained by means of a fixed scale based on the average percent germination of each seed lot. The herbicidal ratings are defined as follows:

0 — No phytotoxicity.
1 — Slight phytotoxicity.
2 — Moderate phytotoxicity.
3 — Severe phytotoxicity.
4 — Plants all dead
- — Not tested.

Individual injury ratings for each plant type are reported in Table II.

Herbicidal solution concentrations of 0.05 percent, and 0.5 percent are substantially equivalent to application rates of 1 pound per acre and 10 pounds per acre, respectively.

TABLE II

| Compound of Example No. | 3 | 4 | 6 | 8 | 9 | 10 |
|---|---|---|---|---|---|---|
| Rate of Application (percent) | 0.5 | 0.5 | 0.5 | 0.5 | 0.5 | 0.5 |
| Plant Species | | | | | | |
| Canada thistle | — | — | — | 2 | 1 | 0 |
| Cocklebur | — | — | 1 | 4 | 1 | 0 |
| Velvetleaf | — | — | 0 | 4 | 0 | 0 |
| Morning glory | 2 | 1 | 1 | 4 | 2 | 0 |
| Lambsquarters | — | — | 3 | 4 | 1 | 4 |
| Nutsedge | — | — | 0 | 1 | 1 | 0 |
| Smartweed | — | — | — | 4 | 3 | 0 |
| Quackgrass | — | — | 1 | 1 | 0 | 0 |
| Johnsongrass | — | — | 0 | 0 | 0 | 0 |
| Brome | 0 | 0 | 0 | 2 | 0 | 1 |
| Barnyard Grass | — | — | 1 | 3 | 2 | 1 |

TABLE II-continued

| Compound of Example No. | 3 | 4 | 6 | 8 | 9 | 10 |
|---|---|---|---|---|---|---|
| Rate of Application (percent) | 0.5 | 0.5 | 0.5 | 0.5 | 0.5 | 0.5 |
| Wild Oat | 0 | 0 | 1 | — | — | — |
| Rye grass | 1 | 0 | 0 | — | — | — |
| Wild buckwheat | 0 | 1 | 3 | — | — | — |
| Radish | 1 | 0 | 2 | — | — | — |
| Sugar beets | 1 | 1 | 4 | — | — | — |
| Foxtail | — | — | 2 | — | — | — |
| Crabgrass | 2 | 0 | 2 | — | — | — |
| Pigweed | 3 | 3 | 4 | — | — | — |
| Soybean | 1 | 1 | 1 | — | — | — |
| Tomato | 0 | 1 | 3 | — | — | — |
| Sorghum | 1 | 0 | 0 | — | — | — |

While this invention has been described with respect to certain embodiments, it is to be understood that it is not so limited and that variations and modifications thereof obvious to those skilled in the art to which this invention appertains can be made without departing from the spirit or scope thereof.

What is claimed is:

1. A compound of the formula

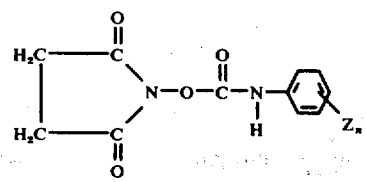

wherein $n$ is 0–3 and Z is halo or lower alkoxy.

2. Compound according to claim 1 wherein $n$ is zero.
3. Compound according to claim 1 wherein $n$ is an integer from 1–3.
4. Compound according to claim 3 wherein Z is halo.
5. Compound according to claim 4 wherein the halogen is o-fluoro.
6. Compound according to claim 4 wherein the halogen is m-chloro.
7. Compound according to claim 4 wherein $n$ is 2 and the Z's are chloro in the 3 and 4 positions.
8. Compound according to claim 3 wherein Z is lower alkoxy.
9. Compound according to claim 8 wherein $n$ is 1 and Z is p-ethoxy.

* * * * *